United States Patent [19]
Holt et al.

[11] Patent Number: 4,954,446
[45] Date of Patent: Sep. 4, 1990

[54] AROMATIC STEROID 5-α-REDUCTASE INHIBITORS

[75] Inventors: Dennis A. Holt, Downington; Mark A. Levy, St. Davids; Brian W. Metcalf, Radnor, all of Pa.

[73] Assignee: SmithKline Beecham Corporation, Philadelphia, Pa.

[21] Appl. No.: 380,226

[22] Filed: Jul. 14, 1989

Related U.S. Application Data

[63] Continuation-in-part of Ser. No. 198,534, May 25, 1988, abandoned.

[51] Int. Cl.$^5$ .................. A61K 31/56; C07J 41/00
[52] U.S. Cl. .................. 435/184; 552/502; 552/548; 552/552; 552/541; 552/546; 552/613; 552/610; 552/554; 552/553; 552/626; 552/611; 552/614; 552/646; 552/627; 552/651; 552/522; 552/532; 552/558; 552/515; 552/539; 540/110; 540/98; 540/28; 540/96; 540/108; 514/176; 514/177; 260/397.1; 260/397.2; 558/57
[58] Field of Search .................. 514/169, 176, 177; 435/184; 260/397.1, 397.2; 558/429, 57

[56] References Cited

U.S. PATENT DOCUMENTS

| | | | |
|---|---|---|---|
| 4,191,759 | 3/1980 | Johnston et al. | 260/397.1 |
| 4,317,817 | 3/1982 | Blohm et al. | 260/397.1 |
| 4,361,578 | 11/1982 | Alia et al. | 558/429 |
| 4,377,584 | 3/1983 | Rasmusson et al. | 540/576 |

OTHER PUBLICATIONS

Cacchi, et al., Tetrahedron Letters, 27(33), 1986, pp. 3931–3934.
Liang, et al., Steroid Biochemistry, vol. 19(1), 1983, pp. 385–390.
Petrow, et al., Steroids 38(2), 1981, pp. 121–140.

*Primary Examiner*—Mukund J. Shah
*Assistant Examiner*—E. C. Ward
*Attorney, Agent, or Firm*—Wayne J. Dustman; Stuart R. Suter; Edward T. Lentz

[57] ABSTRACT

Invented are substituted acrylate analogues of steroidal synthetic compounds, pharmaceutial compositions containing the compounds, and methods of using these compounds to inhibit steroid 5-α-reductase including using these compounds to reduce prostate size. Also invented are intermediates used in preparing these compounds.

14 Claims, No Drawings

AROMATIC STEROID 5-α-REDUCTASE INHIBITORS

FIELD OF THE INVENTION

The present invention relates to certain novel substituted aromatic A ring analogues of steroidal synthetic compounds, pharmaceutical compositions containing these compounds, and methods for using these compounds to inhibit mammalian steroid 5-α-reductase.

DESCRIPTION OF RELATED ART

The class of steroidal hormones known as androgens is responsible for the physical characteristics that differentiate males from females. Of the several organs that produce androgens, the testes produce these hormones in the greatest amounts. Centers in the brain exert primary control over the level of androgen production. Numerous physical manifestations and disease states result when ineffective production control results in excessive androgen hormone production. For example. acne vulgaris, seborrhea, female hirsutism, and benign prostatic hypertrophy are correlated with elevated androgen levels. Additionally, the incidence of male pattern baldness has been associated with high androgen levels.

Testosterone is the principal androgen secreted by the testes and is the primary androgenic steroid in the plasma of males. It now is known that 5-α-reduced androgens are the active hormones in some tissues such as the prostate and sebaceous gland. Circulating testosterone thus serves as a prohormone for dihydrotestosterone (DHT), its 5-α-reduced analogue in these tissues but not in others such as muscle and testis. Steroid 5-α-reductase is a NADPH-dependent enzyme that converts testosterone to DHT. The importance of this enzyme in male development was dramatically underscored by discovery of a genetic steroid 5-α-reductase deficiency in male pseudohermaphrodites. Imperato-McGinley, J., et al., (1979), *J. Steroid Biochem.* 11 637–648.

Recognition of the importance of elevated DHT levels in many disease states has stimulated many efforts to synthesize inhibitors of this enzyme. Several known steroid 5 α-reductase inhibitors have been disclosed.

The first inhibitor described was the 17 B carboxylic acid steroid by Hsia and Voight in 1973. *J. Invest. Dermat.* 62:224–227. A secosteroid was to be described and also has found utility as an affinity label for 5-α-reductase. Robaire, B., et. al., (1977), *J. Steroid Biochem.* 8:307–310. A diazoketone steroid has been reported as a potent, time dependent inhibitor of steroid 5 -α-reductase. Blohm, T. R., et. al. (1980), *Biochem. Biophys. Res. Comm.* 95:273–280; U.S. Pat. No. 4,317,817, Mar. 2, 1982. A group of 4-aza steroid inhibitors of steroid 5 α-reductase were described in U.S. Pat. No. 4,377,584 which issued Mar. 22, 1983, and in Liang, T., et al. (1983), *J. Steroid Biochem.* 19. 385–390. A 6-methylene steroid also has been shown to be a time-dependent inactivator of steroid 5-α-reductase. Petrow, V., et. al. (1981), Steroids 38:121–140.

Other steroid 5-α-reductase inhibitors also have been described. U.S. Pat. No. 4,361,578 which issued June 2, 1986, describes a class of homosteroid enzyme inhibitors. U.S. Pat. No. 4,191,759 discloses amides of 17B carboxy-4-androsten-3-one that are active as steroid 5-α-reductase inhibitors. Japanese Patent Nos. J60146855-A and J60116657-A disclose various aniline derivatives having numerous activities including 5-α-reductase inhibiting activity. Japanese Patent No. I60142941-A discloses phenyl-substituted ketones having 5-α-reductase inhibiting activity and European Patent No. EP173516-A discloses various phenyl substituted amides having similar activity. Shiseido referenced terpene derivatives that are active inhibitors of steroid 5 -α-reductase. Japanese Patent No. No. J59053417-A.

Palladium-catalyzed carbonylation of substituted androstene derivatives has been described. Caachi, S. et. al., (1986) *Tet. Lett.* 27:3931–3934, and Dolle, R. et. al., (1987) *J.C.S. Chem. Comm.* 904–905. No biological activity for the synthesized compounds, however, is disclosed.

SUMMARY OF THE INVENTION

The present invention resides in the discovery that steroid 5-α-reductase is inhibited by certain substituted aromatic A ring analogues of steroidal synthetic compounds. The compounds are potent enzyme inhibitors.

Presently preferred compounds of the invention and compounds used in the invented pharmaceutical compositions and the invented methods include:

17β-(N,N diisopropylcarboxamide) estr-1,3,5(10)-triene-3-carboxylic acid,

17β-(N-butylcarboxamide)-estr-1,3,5(10)-triene-3-carboxylic acid, 17β-(N,N diisopropylcarboxamide) estr-1,3,5(10),16-tetraene-3-carboxylic acid, 17β-(N-butylcarboxamide)-estr-1,3,5(10),16-tetraene-3 carboxylic acid, 17β-(N,N-diisopropylcarboxamide) estr-1,3,5(10),6,8-pentaene-3-carboxylic acid, 17β-(N,N-diisopropylcarboxamide)-2-methyl-estr-1,3,5(10)-triene-3-carboxylic acid, 17β-(N,N-diisopropylcarboxamide)-4-methyl-estr-1,3,5(10)-triene-3-carboxylic acid, 17β-(N,N-diisopropylcarboxamide)-estr-1,3,5(10),6-tetraene-3-carboxylic acid, 17β-(N,N diisopropylcarboxamide)-2-chloroestr-1,3,5(10)-triene-3-carboxylic acid, 17β-(N,N-diisopropylcarboxamide)-4-chloroestr-10)-triene-3 carboxylic acid, 17β-(N,N-diisopropylcarboxamide)-estr-1,3,5(10)-triene-3-acetic acid, 17β-(N t-butylcarboxamide)-estr-1,3,5(10)-triene-3-acetic acid.

In a further aspect of the invention there are provided novel intermediates and novel processes useful in preparing the presently invented 5-α-reductase inhibiting compounds. The invention also is a method for inhibiting -reductase activity in mammals, including humans, that comprises administering internally to a subject an effective amount of a presently invented 5-α-reductase inhibiting compound. Included in the present invention are pharmaceutical compositions comprising a pharmaceutical carrier and compounds useful in the methods of the invention.

DETAILED DESCRIPTION OF THE INVENTION

The presently invented compounds that inhibit 5-α-reductase have the following Formula (1):

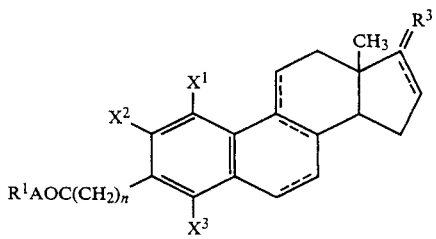

in which:

The B, C, and D rings have optional double bonds where indicated by the broken lines, provided that the does not have a double bond when the B ring has a $C_8$–$C_9$ double bond and the D ring does not have a $C_{16}$–$C_{17}$ double bond when $R^3$ represents two substituents or a divalent substituent;

$X^1$, $X^2$, and $X^3$ are any accessible combination of H, Cl, F, Br, I, $CF_3$, or $C_{1-6}$alkyl. OH, $C_{1-6}$alkoxy, CN, $NO_2$, $N(R^1)$, CHO, or $CO_2R^3$;

A is O or S;

n is 0 or 1;

$R^1$ each independently is H or $C_{1-8}$alkyl; and $R^3$ is (1) α-hydrogen, α-hydroxyl, or
α-acetoxy and/or (a)

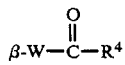

where W is a bond or $C_{1-12}$alkyl and $R^4$ is
(i) hydrogen,
(ii) hydroxyl,
(iii) $C_{1-8}$alkyl,
(iv) hydroxy $C_{1-8}$alkyl,
(v) $C_{1-8}$alkoxy,
(vi) $NR^5R^6$, where $R^5$ and $R^6$ are each independently selected from hydrogen, $C_{1-8}$-alkyl, $C_{3-6}$cycloalkyl, phenyl; or $R^5$ and $R^6$ taken together with the nitrogen to which they are attached represent a 5–6 membered saturated ring comprising up to one other heteroatom selected from oxygen and nitrogen, or
(vii) $OR^7$, where $R^7$ is alkali metal, $C_{1-18}$alkyl, or benzyl, or (b) β-Alk-$OR^8$, where Alk is $C_{1-12}$alkyl, and $R^8$ is
(i) phenyl$C_{1-6}$alkylcarbonyl,
(ii) $C_{5-10}$cycloalkylcarbonyl.
(iii) benzoyl,
(iv) $C_{1-8}$alkoxycarbonyl,
(v) amino, or $C_{1-8}$alkyl substituted amino, carbonyl, or
(vi) $C_{1-8}$alkyl, (2) =CH—W CO—$R^4$ or =CH—W—$OR^8$, where W is a bond or $C_{1-12}$alkyl, and $R^4$ and $R^8$ have the same meaning as above and $R^8$ also is $C_{1-20}$alkylcarbonyl;

(3)

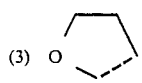

where the dashed bond replaces the 17 α-hydrogen, (4) α-hydrogen and β-$NHCOR^9$ where $R^9$ is $C_{1-12}$alkyl cr $NR^5R^6$ where $R^5$ and $R^6$ have the same meaning as above, (5) α-hydrogen and β-cyano, (6) α-hydrogen and β-tetrazolyl, or (7) keto;

or a pharmaceutically acceptable salt thereof.

As used herein, unless otherwise specified, $C_{1-n}$ alkyl and $C_{1-n}$ alk means a straight or branched hydrocarbon chain having 1 to n carbons, Alk means a straight or branched hydrocarbon chain having 1 to 12 carbons, and "accessible combination" means any combination of substituents that is available by chemical synthesis and is stable.

Preferred among Formula (I) compounds are those in which $X^1$, $X^2$, and $X^3$ are H.

Also, preferred among the presently invented compounds are those having Formula (II):

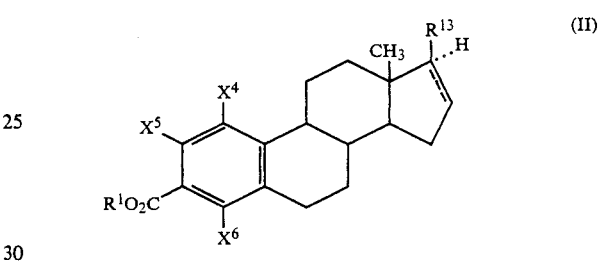

in which:

$X^4$, $X^5$ and $X^6$ independently are H, halo or $C_{1-6}$alkyl;

$R^1$ each independently is H or $C_{1-8}$alkyl; and $R^{13}$ is (a) $CH(CH_3)CH_2OR^1$ or (b) $CONR^1R^1$, or a pharmaceutically acceptable salt thereof.

Particularly preferred are Formula (II) compounds substituted at the 3-position by $CO_2H$.

Also preferred among the presently invented compounds are those having Formula (III):

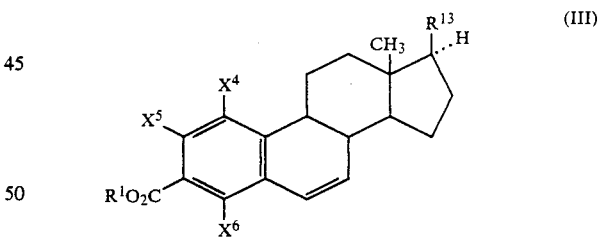

in which $R^1$, $R^{13}$, $X^4$, $X^5$ and $X^6$ are as in Formula (II),

Additionally, preferred among the presently invented compounds are those having Formula (IV):

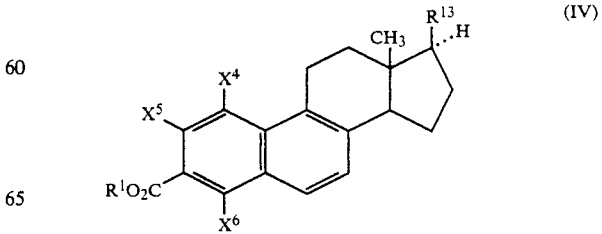

in which $R^1$, $R^2$, and $R^{13}$ are as in Formula (II).

Also preferred are compounds of Formula (I) in which the substituent at position 3 is CH₂CCOH, $X^1$, $X^2$ and $X^3$ is hydrogen and $R^3$ is 17β-(N,N-diisopropylcarboxamide) or 17β-(N-t-butylcarboxamide).

Compounds of Formula (I) are included in the pharmaceutical compositions of the invention and used in the methods of the invention.

As used above and throughout the remainder of the specification and claims, the carbons of the steroid nucleus are numbered and the rings are lettered in standard nomenclature as follows:

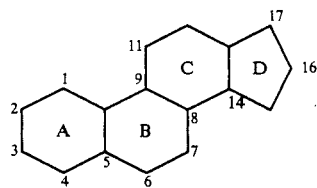

Schemes I and II show formation of Formula (Ia) compounds which are Formula (I) compounds in which R3 is replaced by $R^{14}$ which is $R^3$ or moieties which can be converted to those of $R^3$ by known chemical reactions such as described in 2 J. Fried and J. Edwards, *Organic Reactions in Steroid Chemistry*, Pub: Van Nostrand Reinhold Company (1972). As demonstrated in the following Examples, reactions to convert $R^{14}$ to $R^3$ are performed on products of the synthetic pathway of Schemes I and II or, where appropriate or preferable, on certain intermediates in this synthetic pathway.

Ed. (1983), and exemplified in examples 20–29, below. The formula (a) starting materials are known and readily available or are synthesized from known precursors using known procedures. According to Scheme I, a compound (a) and 2,6-di-tert-butyl-4-methylpyridine in an appropriate organic solvent, preferably dichloromethane, is cooled to +20° C. to 20° C., preferably 0°, and reacted with a trihaloalkyl sulfonic anhydride, preferably trifluoromethane sulfonic anhydride to form compounds (b).

Compounds (b) then are mixed with a palladium (II) compound such as bis(triphenylphosphine)palladium (II) acetate, or, preferably, palladium (II) acetate and a phosphine such as bis(diphenylphosphine)propane, an organic base such as a trialkylamine, preferably triethylamine, a $C_{1-8}$ alkyl alcohol, preferably methanol, in a suitable organic solvent such as dichloroethane and dimethylsulfoxide and heated at 30° C. to 100° C., preferably 70° C., to yield compounds (c), which are Formula (Ia) compounds in which $R^1$ is $C_{1-8}$-alkyl such as methyl. Compounds (c) next are reacted with a suitable base, preferably potassium carbonate, and then acidified to yield compounds (d).

Formula (Ia) compounds unsaturated at $C_{16}$-$C_{17}$ are prepared using modifications of the Scheme I procedure such as exemplified in Example 3 below.

Formula (Ia) compounds in which A is S are prepared from Formula (Ia) compounds in which A is O using standard procedures known to those skilled in the art such as described in Example 18.

SCHEME I

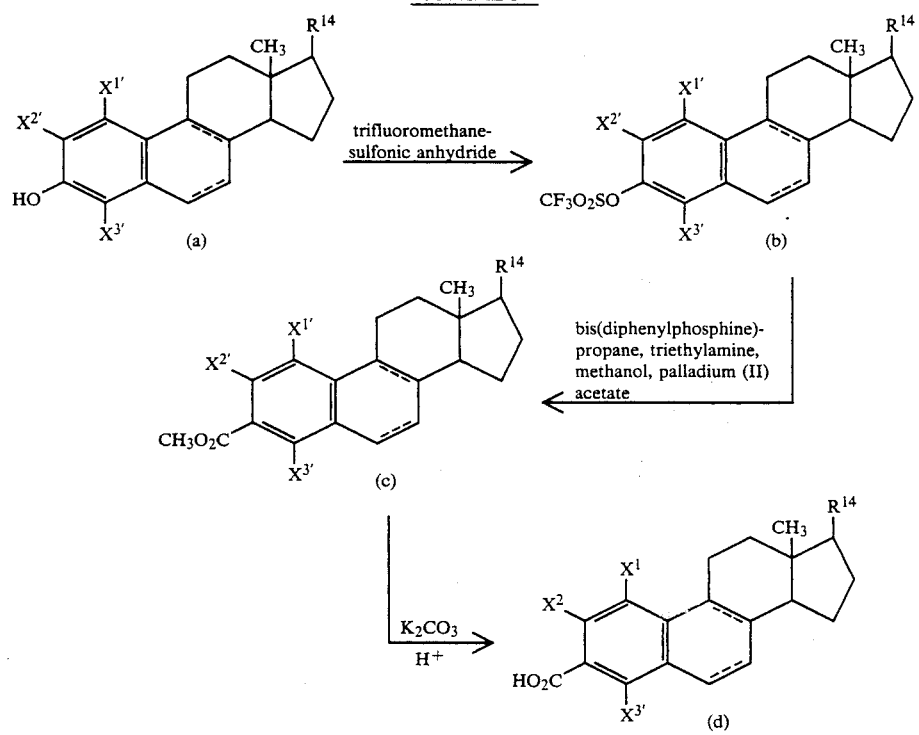

Scheme I depicts formation of Formula (Ia) compounds in which the broken lines indicate optional double bonds; and $X^{1'}$, $X^{2'}$, and $X^{3'}$ are $X^1$, $X^2$, and $X^3$ as in Formula (I) or moieties which can be converted to $X^1$, $X^2$, and $X^3$ by known procedures such as described in Carey and Sundberg, *Advanced Organic Chemistry* 2nd

SCHEME II

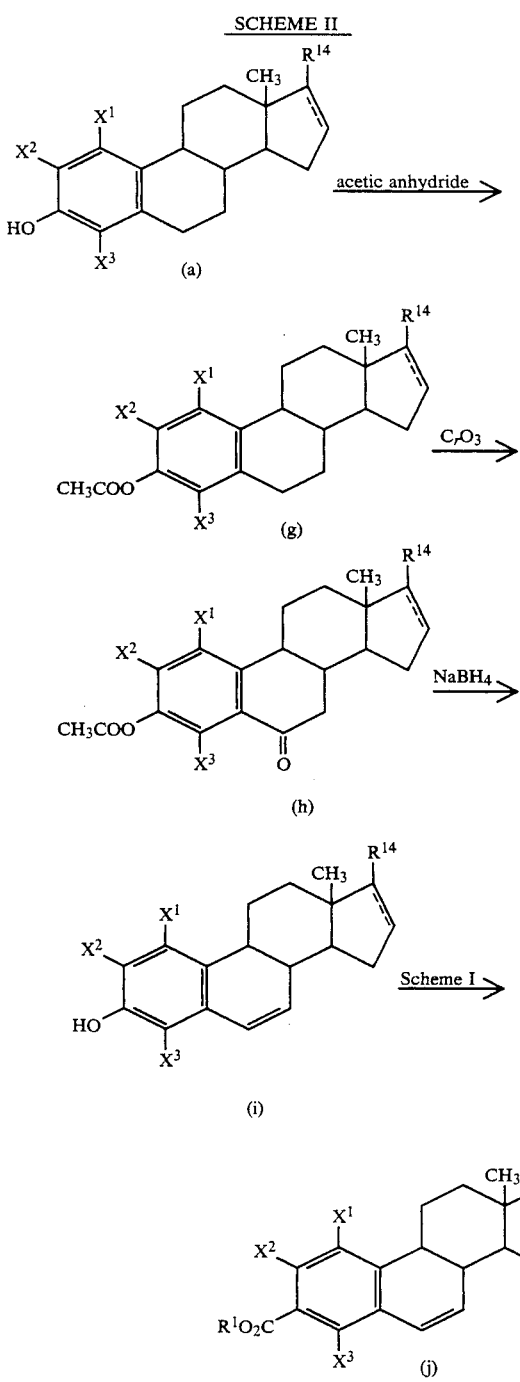

Scheme II outlines formation of Formula (Ia) compounds in which $X^1$, $X^2$, and $X^3$ are as in Formula (I) and the $C_6$-$C_7$ bond is unsaturated. The starting materials for Scheme II are compounds (a) from Scheme I. As outlined in Scheme II, compounds (a) in a suitable organic solvent, such as pyridine, are treated with a $C_{1-8}$alkyl anhydride, such as acetic anhydride to yield formula (g) compounds. Compounds (g) then are treated with an oxidizing agent such as pyridinium chlorochromate preferably chromium trioxide ($CrO_3$) to form compounds (h).

Compounds (i) are prepared by treating compounds (h) with a reducing agent such as lithium aluminum hydride, diisobutylaluminum hydride, or preferably sodium borohydride ($NaBH_4$) Compounds (j), Formula (I) compounds in which the $C_6$-$C_7$ bond is unsaturated, then are prepared as shown in Scheme I.

Formula (Ia) compounds unsaturated at $C_9$-$C_{11}$ are prepared using modifications of the Scheme I and II processes which will be readily apparent to those skilled in the art who aware of these schemes. An example of such a modification is shown in example 19.

Formula (I) compounds where n is 1 are prepared by reacting the trifluoromethylsulfonate intermediates (Formula V) with tributylvinylstannane and a palladium (II) catalyst to the corresponding 3-ethenyl derivative. Treatment with 9-borobicyclononane or like reagent followed by hydrogen peroxide gives the 3-hydroxyethyl derivative which is further oxidized to the 3-acetic acid compounds Pharmaceutically acceptable acid addition salts of the compounds of the invention containing a basic group are formed where appropriate with strong or moderately strong organic or inorganic acids in the presence of a basic amine by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the acid addition salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases include nontoxic alkali metal and alkaline earth bases, for example, calcium, sodium, and potassium hydroxide; ammonium hydroxide, and nontoxic organic bases such as triethylamine, butylamine, piperazine, and (trihydroxymethyl)methylamine.

In preparing the presently invented compounds of Formula (I), novel intermediates of the following Formula (V) are synthesized.

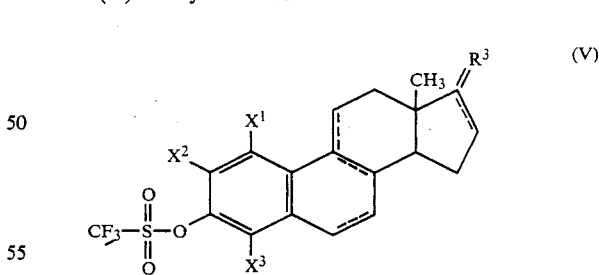

in which:

the B, C, and D ring double bonds, $X^1$, $X^2$, and $X^3$, are as defined in Formula (I), $R^3$ is as defined in Formula (I) except $R^3$ is not keto when Xl, $X^2$, and $X^3$ are hydrogen.

Because Formula (I) compounds inhibit steroid 5 α-reductase activity, they have therapeutic utility in treating diseases and conditions wherein decreases in DHT activity produce the desired therapeutic effect. Such diseases and conditions include acne vulgaris, seborrhea, female hirsutism, prostate diseases such as benign prostatic hypertrophy, and male pattern baldness.

The potency of several compounds of the invention was tested for potency in inhibiting human steroid 5-α-reductase using tissue from hyperplastic human prostates. In determining potency in inhibiting the human enzyme, the following procedure was employed:

Frozen human prostates were thawed and minced into small pieces (5 mm$^3$). The tissue was homogenized in 3 to 5 volumes of 20 mM potassium phosphate, pH 6.5, buffer containing 0.33 M sucrose, 1 mM dithiothreitol, and 50 μM NADPH with a Brinkmann Polytron (Sybron Corporation. Westbury, N.Y.). The solution was subjected to sonication for 3 to 5 minutes with a Sonifier (Branson Sonic Power Co.) followed by hand homogenization in a glass to glass Dounce homogenizer (Kontes Glass Company, Vineland, N.J.).

Prostatic particles were obtained by differential centrifugation at 600 or 1000×x g for 20 minutes and 140,000×q for 60 minutes at 4° C. The pellet obtained from the 140,000×g centrifugation was washed with 5 to 10 tissue volumes of the buffer described above and recentrifuged at 140,000×q. The resulting pellet was suspended in 20 mM potassium phosphate buffer, pH 6.5, containing 20% glycerol, 1 mM dithiothreitol, and 50 μM NADPH. The suspended particulate solution was stored at −80° C.

A constant amount of [$^{14}$C]-testosterone (52 to 55 mCi/mmol, New England Nuclear, Boston, Mass.) in ethanol and varying amounts of the potential inhibitor in ethanol were deposited in test tubes and concentrated to dryness in SAVANT Speed Vac. To each tube was added buffer, 20 μl of 10 mM NADPH and an aliquot of prostatic particulate solution to a final volume of 0.5 ml of 50 mM sodium citrate, pH 5.0. After incubating the solution at 37° C for 20 to 30 minutes the reaction was quenched by the addition of 4 ml ethyl acetate and 0.25 μmol each of testosterone, dihydrotestosterone, androstanediol, and androstanedione as carriers. The organic layer was removed to a second test tube and evaporated to dryness in vacuo. The residue was dissolved in 20 to 30 μl chloroform, spotted on an individual lane of a 20×20 cm prechannelled silica gel TLC plate (Si 250F-PA, Baker Chemical) and developed twice with acetone:chloroform (1:9). The radiochemical content in the bands of the substrate and the products was determined with a BIOSCAN Imaging Scanner (Bioscan, Inc., Washington, D.C.). The percent of recovered radiolabel converted to product was calculated, from which enzyme activity was determined. All incubations were conducted such that no more than 12% of the substrate (testosterone) was consumed.

The experimentally obtained data was computer fitted to a linear function by plotting the reciprocal of the enzyme activity (1/velocity) against the variable inhibitor concentration (Dixon, M. (1953), *Biochem. J.*, 55, 170). Assuming that the steroidal inhibitor is a competitive inhibitor against testosterone, a value for the inhibition constant ($K_i$) can be calculated from equation 1:

$$K_i = (B/A)/ S/K_m + 1) \qquad 1$$

where B is the intercept on the 1/velocity axis, A is the slope of the line, S is the concentration of substrate (testosterone) used in the experiment, and $K_m$ is the Michaelis Menton constant of the substrate (testosterone) determined in a separate experiment to be 4.5 μM.

Table II displays the results of the above testing and shows that the tested compounds of the invention are potent inhibitors of human steroid 5 -60 -reductase.

Table II

Inhibition Constants of Human Prostatic Steroid 5-α-Reductase

TABLE II

| Inhibition Constants of Human Prostatic Steroid 5-α-Reductase | |
|---|---|
| Compound | $K_i$(nM) |
| 17β-(N,N-Diisopropylcarboxamide)-estr-1,3,5(10)-triene-3-carboxylic Acid | 19 |
| 17β-(N-tert-Butylcarboxamide)-estr-1,3,5(10-triene-3-carboxylic Acid | 43 |
| 17β-(N,N-Diisopropylcarboxamide)-estr-1,3,5(10),6,8-pentaene-3-carboxylic Acid | 40 |
| 17β-(N,N-Diisopropylcarboxamide)-estr-1,3,5(10),6-tetraene-3-carboxylic Acid | 30 |
| 17β-(N,N-Diisopropylcarboxamide)-estr-1,3,5(10),16-tetraene-3-carboxylic Acid | 70 |
| 17β-(N-tert-Butylcarboxamide)-estr-1,3,5(10),16-tetraene-3-carboxylic Acid | 60 |
| 17β-(N,N-Diisopropylcarboxamide)-2-methyl-estr-1,3,5(10)-triene-3-carboxylic Acid | 57 |
| 17β-(N,N-Diisopropylcarboxamide)-4-methyl-estr-1,3,5(10)-triene-3-carboxylic Acid | 270 |
| 17β-(N-N-diisopropylcarboxamide)-estr-1,3,5(10)-triene-3-acetic acid | 20 |

One of the compounds of the invention, 17β (N-tert-butylcarboxamide)-estr-1,3,5(10)-triene 3-carboxylic acid, also was tested for its in vivo potency in inhibiting steroid 5-α-reductase activity. Male Charles River CD rats, 48 days old, weighing approximately 200 gm were administered this compound dissolved in propylene glycol and diluted in normal saline. Following compound administration the animals were sacrificed, the ventral prostates were excised, and DHT levels were measured by the following procedure.

Prostate tissue was excised, trimmed, weighed, minced and washed with phosphate buffer. The tissue then was homogenized in phosphate buffer and extracted by addition of ethyl acetate and mixing on an orbital mixer for forty-five minutes. The ethyl acetate was evaporated, the residue was reconstituted in ethanol, and was centrifuge filtered using 0.45 μM filter paper. The components then were separated using reverse-phase HPLC collecting the DHT fraction. The fraction was reduced to dryness and in standard DHT assay buffer available from reconstituted Amersham. DHT levels then were measured using standard techniques such as radioimmunoassay.

In the compound-treated rats, prostatic DHT levels were decreased forty percent relative to vehicle treated controls (p<15) four hours after compound administration at a dose of 20mg/kg.

The compounds of Formula (I) are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the present compounds of Formula (I) in a pharmaceutical dosage unit as described above will be an efficacious, nontoxic quantity selected from the range of 0.1–1000 mg/kg of active compound, preferably 1–100 mg/kg. The selected dose is administered to a human patient in need of steroid 5 α-reductase inhibition from 1–6 times daily, topically, orally, rectally, by injection, or continuously by infusion. Oral dosage units for human administration preferably contain from 1 to 500 mg of active compound. Parenteral administration, which uses lower dosages is preferred. Oral administration at higher dosages, however, also can be used when safe and convenient for the patient.

The invented methods of inhibiting steroid 5-α-reductase activity in mammals, including humans, comprises administering internally to a subject an effective steroid 5-α-reductase inhibiting amount of a compound of Formula (I). The invented methods of reducing prostate size which include methods of reducing the rate at which prostate size increases comprise administering internally to a subject as effective amount of a Formula (I) compound.

Contemplated equivalents of Formula (I) compounds include compounds that, upon administration to mammals, including humans, are metabolized to Formula (I) compounds or metabolized to Formula (I) compound active metabolites at a sufficient rate and in sufficient amounts to produce physiologic activity of Formula I compounds. Such compounds also would be included in the invented pharmaceutical compositions and used in the invented methods.

The following examples illustrate preparation of Formula (I) compounds and pharmaceutical compositions containing these compounds. The examples are not intended to limit the scope of the invention as defined hereinabove and as claimed below.

EXAMPLE 1

17β-(N,N Diisopropylcarboxamide) estr 1,3,5(10)-triene-3-carboxylic Acid.

(i) 3,17 Di-(trifluoromethylsulfonate)-estr 1,3,5(10),16-tetraene. Estrone (16.2 q, 60 mmol) and 2,6-di-tert-butyl-4-methylpyridine (27 g, 130 mmol) was dissolved in 500 mL of dicholoromethane and the solution was cooled to 0° C. Trifluoromethane sulfonic anhydride (45.3 g,160 mmol) then was slowly added to the solution. The resulting solution was stirred at 0° C for 2 hours and then at 25° C. for 4 hours. The solution then was washed with 10% aqueous hydrochloric acid (HCl), saturated aqueous sodium bicarbonate (NaHCO3), brine, and then dried and concentrated. Chromatography (silica gel, 5% ethyl acetate (EtOAc) in hexane) afforded 25.3 q (79%) of 3,17 di(trifluoromethylsulfonate) estr 1,3,5(10),16-tetrane.

(ii) 17 (N,N Diisopropylcarboxamide) 3-(trifluoromethylsulfonate) estr-1,3,5(10),16 tetraene.

A mixture of 3,17 di-(trifluoromethylsulfonate) estr 1,3,5(10),16 tetraene (14 g, 26 mmol), palladium(II) acetate (500 mg), triphenylphosphine (1.1g), triethylamine (9 mL), diisopropylamine (50 mL), and dimethylformamide (100 mL) was heated at 60° C. under an atmosphere of carbon monoxide for 5 hours. The mixture was concentrated, diluted with water, and thoroughly washed with dichloromethane. The combined organic extracts were then washed with 10% aqueous HCl, saturated aqueous NaHCO3, dried, and concentrated to a dark oil. Chromatography of the oil on silica gel (15% EtOAc in hexane) afforded 8 g (59%) of 17-(N,N diisopropylcarboxamide) 3-(trifluoromethylsulfonate)-estr-1,3,5(10),16-tetraene as a white powder.

(iii) 3-Carbomethoxy-17-(N,N-diisopropylcarboxamide)-estr-1,3,5(10),16-tetraene.

A mixture of 17 (N,N diisopropylcarboxamide)-3 (trifluoromethylsulfonate) estr-1,3,5(10),16-tetraene (8.3 q, 16 mmol), palladium(II) acetate (224 mg), 1,3-bis(diphenylphospine)propane (410 mg), triethylamine (4.5 mL), methanol (32 mL), 1,2-dichloroethane (17 mL), and dimethylsulfoxide (50 mL) was heated at 70° C. for 5 hours under a carbon monoxide atmosphere. The cooled reaction mixture then was diluted with chloroform and washed with water, 10% aqueous HCl, saturated aqueous NaHCO3, and brine and then concentrated. The residue was chromatographed (silica gel, 20% EtOAc in hexane) to yield 5 g (73%) of 3-carbomethoxy 17 (N,N diisopropyl-carboxamide) estr-1,3,5(10),16-tetraene.

(iv) 3 Carbomethoxy-17β-(N,N diisopropylcarboxamide) estr 1,3,5(10)-triene

3-Carbomethoxy-17-(N,N diisopropylcarboxamide) estr-1,3,5(10),16-tetraene (7.4g. 17.5 mmol) dissolved in 125 mL EtOAc and 45 mL ethanol was hydrogenated over platinum oxide (800 mg) at 1 atm. for 3 hours. The catalyst was removed by filtration and the filtrate concentrated to yield 6 g (81%) of 3 carbomethoxy-17-β-(N,N-diisopropylcarboxamide)-estr-1,3,5(10)-triene.

(v) 17β-(N,N-Diisopropylcarboxamide)-estr-1,3,5(10)-triene-3-carboxylic Acid.

3 Carbomethoxy-17β-(N,N-diisopropylcarboxamide) estr-1,3,5(10)-triene (93 mg, 0.2 mmol) and mg potassium carbonate suspended in 3 ml of 10:1 methanol water were heated at reflux for 18 hours. The mixture then was acidified with 10% HCl, diluted with water, and thoroughly extracted with chloroform. Concentration of the chloroform extracts followed by recrystallization from acetone yielded 81 mg (90%) of -(N-N diisopropylcarboxamide)-estr-1,3,5(10) triene carboxylic acid as a white solid, m.p.233°–234° C.

EXAMPLE 2

17β (N-tert-Butylcarboxamide) estr 1,3,5(10)-triene-3 carboxylic Acid.

The title compound (m.p. 235°–240° C. from acetone) was prepared according to Example 1 (ii through v) by substituting tertbutylamine for diisopropylamine.

EXAMPLE 3

17β-(N,N Diisopropylcarboxamide) estr-1,3,5(10),16 tetraene 3-carboxylic Acid.

The title compound (m.p. 225°–234° C.) was prepared according to Example 1 (v) by substituting 3-carbomethoxy-17-(N,N-diisopropylcarboxamide) estr 1,3,5(10),16-tetraene for 3-carbomethoxy-17β (N,N diisopropyl carboxamide)-estr-1,3,5(10)triene.

EXAMPLE 4

7β-(N-tert Butylcarboxamide)-estr 1,3,5(10),-16 tetraene 3 carboxylic Acid

The title compound (m.p. 212°-215° C. from acetonitrile) was prepared according to Example 1 (v) by substituting 3-carbomethoxy-17 (N-tert-butylcarboxamide) estr-1,3,5(10),-16-tetraene (prepared as in Example 2) for 3-carbomethoxy-17β-(N,N diisopropylcarboxamide)-estr-1,3,5(10)-triene.

EXAMPLE 5

17β-(N,N-Diisopropylcarboxamide) estr-1,3,5(10),-6,8-pentaene-3-carboxylic Acid.

The title compound (m.p. 257°-260° C. from acetonitrile) was prepared according to Example 1 by substituting equilenin (1,3,5(10)6,8-estrapentaen-3-ol-17-one) for

EXAMPLE 6

17β-(N,N-Diisopropylcarboxamide) 2-methyl-estr-1,3,5(10)-triene-3-carboxylic Acid.

The title compound (m.p. 272°-273° C.) was prepared according to Example 1 by substituting 2 methylestrone for estrone. 2-Methylestrone was prepared according to the procedure described by Kaneko, Hashimoto, and Kobayashi, Chem. Pharm Bull.. 12, 196(1964) and by Patton, J. Org. Chem. 25,2148 (1960).

EXAMPLE 7

17⊕-(N,N-Diisopropylcarboxamide)-4-methyl estr-1,3,5(10)-triene-3 carboxylic Acid (i) 4-methyl-4-estrene-3,17-dione.

A solution of 4 methyl 4-estrene-3-one-17β-ol (4-methyl 19-nor testosterone prepared according to the procedure described by Atwater, J. Amer. Chem Soc. 82 2847 (1960).; 12 g, 43.8 mmol) in 400 mL dichloromethane was added to a stirred solution of pyridinium chlorochromate (pcc, 14.2g, 66 mmol) in 400 mL dichloromethane. After two hours the mixture was filtered and the filtrate was treated with silica gel and charcoal, filtered and concentrated. Trituration of the residue with cold acetone afforded 6.5 g (54%) of 4 methyl-4-estrene-3,17 dione (ii) 4-Methyl estrone.

A mixture of 4-methyl-4 estrene-3,17 dione (2 q, 7 mmol) and 2 g 10% palladium on carbon in 100 mL of p cymene was heated at reflux for 4 hours. The hot mixture then was filtered and the filtrate was concentrated to yield 900 mg of the crude 4 methyl estrone which was used in the next step without further purification.

(iii) 17β-(N,N Diisopropylcarboxamide) 4-methyl-estr-1,3,5(10)-triene-3-carboxylic Acid.

The title compound (m.p. 271°-273° C. after methanol trituration) was prepared according to Example 1 by substituting 4-methyl-estrone for estrone.

EXAMPLE 8

17β-(N,N-Diisopropylcarboxamide)-estr-1.3.5(10),6-tetraene-3-carboxylic Acid.

(i) N,N-Diisopropyl 3-Methoxy-estr-1,3,5(10)-triene 17β-carboxamide.

The title compound was prepared according to Example 1 (i, ii, and iv) by substituting 3 methyl-estrone for estrone.

(ii) N,N-Diisopropyl Estr-1,3,5(10)-triene-3 ol-17β-carboxamide.

To a 0° C. solution of N,N-diisopropyl 3-methoxy estr-1,3,5(10)-triene 178 carboxamide (4.8 q, 12 mmol) in dichloromethane (150 mL) was added a dichloromethane solution of boron tribromide (45 mL, 1 M, 45 mmol). The resulting solution was stirred at 0° C., for 2 hours and then at 25° C for 30 minutes. After cooling back to 0° C., methanol (50 mL) was added carefully and the volatiles were then removed in vacuo. The residue was redissolved in dichloromethane and washed with water, dried, treated with silica gel and charcoal, filtered and concentrated. Trituration of the residue with acetone afforded 4.7 g (98%) of N,N diisopropyl-estr 1,3,5(10)- triene-3-ol-17β-carboxamide as a white solid.

(iii) N,N Diisopropyl Estr-1,3,5(10)-triene-3-acetoxy-178-carboxamide.

A solution of N,N-diisopropyl estr-1,3,5(10)-triene-3 ol-173-carboxamide (4.7 g, 12.3 mmol) in 100 mL pyridine was treated with 70 mL acetic anhydride for 18 hours. The reaction mixture was poured into ice water and extracted with ethyl acetate. The organic extract was washed with 10% aqueous HCl, water, brine, and concentrated to afford 5.2 g (100%) of N,N diisopropyl estr-1,3,5(10)-triene-3-acetoxy-17β-carboxamide.

(iv) N,N Diisopropyl 6 Oxo-estr 1,3,5(10)-triene-3-acetoxy-17β-carboxamide.

To a solution of N,N-diisopropyl estr-1,3,5(10)-triene-3-acetoxy-17β-carboxamide (5 q, 12 mmol) in 17 mL glacial acetic acid was added a solution of chromium trioxide (3.5 q) in 23 ml acetic acid and 4 mL water. After stirring for 18 hours, ethanol (20 mL) was added and the resulting mixture was extracted with ethyl ether. The ethereal extract was washed with water, saturated aqueous NaHCO₃, dried over sodium sulfate, and concentrated. Chromatography (silica gel, 25% EtOAc in 1,3,5(10) triene-3-acetoxy-17β-carboxamide, m.p. 223°-224° C. (recrystallized from methanol).

(v) N,N Diisopropyl Estr-1,3,5(10),6-tetraene-3 ol-178-carboxamide.

A suspension of N,N-diisopropyl 6 oxo estr-1,3,5(10) triene-3-acetoxy-17β-caboxamide (400 mg, 0.9 mmol) in 40 mL methanol at 15° C was treated with 800 mg of NaBH4 for 1 hour. HCl (3.5 mL) and water (3.5 mL) was added and the resulting mixture was heated at reflux for 1 hour. The mixture was cooled, diluted with water and extracted with ethyl acetate. The organic extract was washed with water, brine, dried, and concentrated to a solid. Chromatography (silica gel, 5% EtOAc in methylene chloride) afforded 200 mg (58%) of N,N-diisopropyl estr-1,3,5(10), 6-tetraene-3 ol 17β-carboxamide, m.p. 276°-279° C.

(vi) 17β-(N,N Diisopropylcarboxamide)-3-(trifluoromethylsulfonate)-estr 1,3, 5(10),6 tetraene.

The title compound was prepared according to Example 1 (i) by substituting N,N-diisopropyl estr 1,3,5(10),6 tetraene-3-ol-17β-carboxamide for estrone.

(vii) 3 Carbomethoxy 178 (N,N-diisopropylcarboxamide)-estr-1,3,5(10),6-tetraene.

The title compound (m.p. 183°-185° C., triturated with methanol) was prepared according to Example 1 (iii) by substituting 178-(N,N-diisopropyl-carboxamide)-3-(trifluoromethylsulfonate)-estr-1,3,5(10),6-tetraene for 17B (N,N diisopropylcarboxamide)-3 (trifluoromethylsulfonate) estr 1,3,5(10),16 -tetraene.

(viii) 17β-(N,N-Diisopropylcarboxamide) estr-1,3,5(10),6 tetraene 3 carboxylic Acid.

The title compound (m.p. 209°–210° C., recrystallized from EtOAc-hexane) was prepared according to Example 1 (v) by substituting 3-carbomethoxy 17β-(N,N-diisopropylcarboxamide)-estr-1,3,5(10),6-tetraene for 3-carbomethoxy 17β-(N,N-diisopropylcarboxamide)-estr-1,3,5(10) triene.

EXAMPLE 9

17β-(N,N-Diisopropylcarboxamide)-2-chloro-estr-1,3,5(10)-triene 3 carboxylic Acid and 17β-(N,N Diisopropylcarboxamide)-4-chloro estr-1,3,-5(10)-trien-3-carboxylic Acid.

(i) 17β-(N,N-Diisopropylcarboxamide)-3-(4,4 dimethyl-2-oxazolinyl)-estr-1,3,5(10) triene.

A solution of 17B (N,N diisopropylcarboxamide)-estr 1,3,5(10)-triene-3-carboxylic acid (2.07 g, 5.04 mmol), thionyl chloride (0.73 mL, 10.0 mmol) and dichloromethane (104 mL) was stirred at room temperature for 2 hours. The solution then was concentrated at 50° C. on a rotary evaporator and the resultant acid chloride dissolved in 30 mL of dichloromethane. The acid chloride solution was added slowly at 0° C. to a solution of 2-amino-2 methyl-1 propanol (0.897 g, 10.1 mmol) in 20 mL of dichloromethane. The mixture was stirred at room temperature for several hours then washed twice with water, dried, and concentrated to 2.26 g of a benzamide. Thionyl chloride (5.0 mL, 69 mmol) slowly was added to the benzamide and the resultant yellow solution was stirred at ambient temperature for 10 minutes, then diluted with 100 mL of petroleum ether. The solvent was decanted from the gummy precipitate and the precipitate was washed with additional petroleum ether. The precipitate was suspended in water which was made basic with 10% sodium hydroxide and extracted with dichloromethane. The extract was washed with water, dried and concentrated to 1.85 g (79%) of 17β-(N,N diisopropylcarboxamide) 3 (4,4 dimethyl-2-oxazolinyl)-estr-1,3,5(10)-triene as a tan foam.

(ii) 17β-(N,N-Diisopropylcarboxamide)-3-(4,4-dimethyl-2-oxazolinyl)-2-chloro-estr-1,3,5(10)-triene and 17β-(N,N-Diisopropylcarboxamide-3-(4,4-dimethyl-2-oxazolinyl)-4-chloro-estr-1,3,5(10)-triene.

A solution of 17β-(N,N-diisopropylcarboxamide)-3-(4,4-dimethyl-2-oxazolinyl)-estr-1,3,5(10)-triene (1.18 g, 2.54 mmol) in dry tetrahydrofuran (THF) (59 mL) was cooled in an ice bath under an argon atmosphere and treated successively with N,N,N',N'-tetramethylethyenediamine (0.84 mL, 5.6 mmol) and 2.5M n-butyllithium in hexane (2.23 mL, 5.59 mmol). The reddish-brown solution was stirred in the cold for 5 minutes, then a solution of hexachloroethane (1.32 g, 5.55 mmol) in 24 ml of THF was added rapidly. After stirring for 5 minutes the cooling bath was removed and stirring continued for 30 minutes. The mixture then was diluted with water and extracted twice with ethyl ether. The combined ether extracts were washed three times with water, dried, and concentrated to 1.95 g of crude product. Chromatography (silica gel, 25% EtOAc in hexane) yielded 1.16 g of a mixture of 17β-(N,N-diisopropylcarboxamide)-3-(4,4-dimethyl-2-oxazolinyl)-estr-1,3,5(10)-triene (ca. 49%), 17β-(N,N-diisopropylcarboxamide)- 3 -(4,4-dimethyl-2-oxazolinyl-4-chloro-estr-1,3,5(10)-triene (ca. 31%), and 17β-(N,N-diisopropylcarboxamide)-3-(4,4-dimethyl-2-oxazolinyl-4-chloro estr-1,3,5(10)-triene (ca 15%) which was used in the next step without further purification.

(iii) 17β-(N,N-Diisopropylcarboxamide)-2-chloro-estr-1,3,5(10)-triene-3-carboxylic Acid and 17β-(N,N-Diisopropylcarboxamide)-4-chloro-estr-1,3,5(10)-triene-3-carboxylic Acid.

A solution of 0.58 g of mixture of 17β-(N,N-diisopropylcarboxamide-3-(4,4-dimethyl-2-oxazolinyl)-estr-1,3,5(10)-triene (ca. 49%), 17β-(N,N-diisopropylcarboxamide)-3-(4,4-dimethyl-2-oxazolinyl)-2-chloro estr-1,3,5(10)-triene (ca. 31%), and 17β-(N,N-diisopropylcarboxamide)-3-(4,4-dimethyl-2-oxazolinyl)-4-chloro-estr 1,3,5-(10)-triene (ca. 15%) in 227 mL THF and 227 mL 10% HCl was heated at reflux for 4 hours and then concentrated to remove most of the THF. An additional 76 mL of 10% HCl was added and the reflux continued overnight. The resultant dark mixture was cooled and extracted twice with dichloromethane. The combined extracts were washed with water, dried and concentrated to 1.03 q of dark gummy oil. Preparative high pressure liquid chromatography (silica gel, 12 5% EtOAc, 0.5% formic acid in hexane) provided 60.6 mg of 17β-(N,N-diisopropylcarboxamide)-2-chloro estr-1,3,5(10)-triene-3-carboxylic acid (m.p. 301°–305° C., dec.) and 29 mg of 17β-(N,N-diisopropylcarboxamide)-4-chloro-estr-1,3,5(10)-triene-3-carboxylic acid (m.p. 262°–265° C., dec.).

EXAMPLE 10

Estr-1,3,5(10)-triene-17-one-3-carboxylic Acid (i) 3-(Trifluoromethylsulfonate)-estr-1,3,5(10)-triene-17-one.

Estrone is dissolved in dichloromethane, cooled to 0°, and treated with 2,6-lutidine and trifluoromethane sulfonic anhydride for two hours. Aqueous workup yields 3-(trifluoromethylsulfonate)-estr-1,3,5(10)-triene-17-one.

(ii) Methyl Estr-1,3,5(10)-triene-17-one-3-carboxylate.

The title compound is prepared according to Example 1 (iii) by substituting 3-(trifluoro methylsulfonate)-estr-1,3,5(10)-triene-17-one for 17-(N,N-diisopropylcarboxamide)- 3-(trifluoromethylsulfonate)-estr-1,3,5(10),16-tetraene.

(iii) Estr-1,3,5(10)-triene-17-one-3-carboxylic Acid.

The title compound is prepared according to Example 1(v) by substituting methyl estr-1,3,5(10)-triene-17-one-3-carboxylate for 3-carbomethoxy-17β-(N,N-diisopropylcarboxamide)-estr-1,3,5(10)-triene.

EXAMPLE 11

Ethyl 19-Nor-pregn-1,3,5(10),17(20)-tetraene-3-carboxy-21-oate

A solution of sodium ethoxide (680 mg, 10 mmol) in 5 mL ethanol is added to a mixture of estr-1,3,(5)10-triene-17-one-3-carboxylic acid (894 mg, 3 mmol) and methyl diethylphosphonoacetate (2.12 g, 10 mmol) and the resulting mixture heated at reflux for four hours The mixture is cooled, concentrated, diluted with dilute acetic acid and washed with ether. The combined ethereal extracts are washed with water and brine, and concentrated to yield ethyl 19-nor-pregn-1,3,5 (10),17(20)-tetraene-3-carboxy-21-oate.

EXAMPLE 12

19-Nor-pregn-1,3,5(10)-triene-3-carboxy-21-oate

The title compound is prepared according to Example 1 (iv,v) by substituting ethyl 19-nor-pregn-1,3,5(10),17(20)-tetraene-3-carboxy-21-oate for 3-carbomethoxy-17-(N,N-diisopropylcarboxamide)-estr-1,3,5(10),16-tetraene.

EXAMPLE 13

Estr-1,3,5(10)-triene-3,17β-dicarboxylic Acid (i) 3-Carbomethoxy-estr-1,3,5(10),16-tetraene-17-(trifluoromethyl-sulfonate).

The title compound is prepared according to Example 1 (i) by substituting methyl estr-1,3,5(10)-triene-17-one-3-carboxylate for estrone.

(ii) 3-Carbomethoxy estr-1,3,5(10),16-tetraene-17-carboxylic Acid.

The title compound is prepared according to Example 1 (ii) by substituting 3-carbomethoxy-estr-1,3,5(10),16-tetraene-17-(trifluoromethylsulfonate) for 3,17-di-(trifluoromethylsulfonate)-estr-1,3,5(10),16-tetraene and substituting formic acid for diisopropylamine.

(iii) 3-Carbomethoxy-estr-1,3,5(10)-triene-17β-carboxylic Acid.

The title compound is prepared according to Example 1 (iv) by substituting 3-carbomethoxy-estr-1,3,5(10),16-tetraene-17-carboxylic acid for 3-carbomethoxy-17-(N,N-diisopropylcarboxamide)-estr-1,3,5(10),16-tetraene.

(iv) Estr-1,3,5(10)-triene-3,17β-di-carboxylic Acid.

The title compound is prepared according to Example 1 (v) by substituting 3-carbomethoxy-estr-1,3,5(10)-triene-17β-carboxylic acid for 3-carbomethoxy-17β-(N,N-diisopropylcarboxamide)-estr-1,3,5-(10)-triene.

EXAMPLE 14

Estr-1,3,5(10)-triene-17β-carboxyaldehyde-3-carboxylic Acid (i) 3-Carbomethoxy-estr-1,3,5,(10)-triene-17β-carboxychloride A solution of 3-carbomethoxy-estr-1,3,5(10)-triene-17β-carboxylic acid (1 mmol) is suspended in 10 mL toluene and treated with 0.5 mL of oxalyl chloride for two hours. The volatile materials then are removed in vacuo leaving a residue of 3-carbomethoxy-estr-1,3,5(10)-triene-17β-carboxychloride.

(ii) 3-Carbomethoxy-estr-1,3,5(10)-triene-17β-carboxaldehyde.

A solution of 3-carbomethoxy-estr-1,3,5(10)-triene-17β-carboxychloride (1 mmol) in 10 mL tetrahydrofuran is treated with lithium tri-t-butoxy-aluminum hydride (1 mmol) at 0° C. for one hour to yield, After aqueous workup, 3-carbomethoxy-estr-1,3,5(10)-triene-17β-carboxaldehyde.

EXAMPLE 15

Estr-1,3,5(10)-triene-17β-(1-oxobutyl)-3-carboxylic Acid (i) 3-carbomethoxy-estr-1,3,5(10)-triene-17β-(1-oxobutyl).

A solution of 3-carbomethoxy-estr-1,3,5(10)-triene-17β-carboxychloride (1 mmol) in 10 mL tetrahydrofuran is treated with 1.0 mmol of di-n-butyl copperlithium at −78° C. The reaction is quenched with aqueous ammonium chloride. Extraction with dichloromethane followed by concentration of the organic extracts and chromatography of the residue yields 3-carbomethoxy-estr-1,3,5(10)-triene-17β-(1-oxobutyl).

(ii) Estr-1,3,5(10)-triene-17β-(1-oxobutyl)-3-carboxylic Acid.

The title compound is prepared according to Example 1 (v) by substituting 3-carbomethoxy-estr-1,3,5(10)-triene-17β-(1 oxobutyl) for 3-carbomethoxy-17β-(N,N-diisopropylcarboxamide)-estr-1,3,5(10)-triene.

EXAMPLE 16

Estr-1,3,5(10)-triene-17α-ol-3,17β-di-carboxylic Acid (i) 17β-cyano-17α-acetoxy-estr-1,3,5(10)-triene-3-(methyl carboxylate).

Methyl estr-1,3,5(10)-triene-17-one-3-carboxylate (10g) is dissolved by warming in 15 mL of acetone cyanohydrin. The crystals which form are filtered, washed with pentane, and then dissolved in a mixture of pyridine (25 mL) and acetic anhydride (25 mL). After 48 hours the volatiles are removed under reduced pressure. The residue is then dissolved in ethyl acetate and washed successively with 5% HCl and aqueous $N_2HCO_3$. The organic solution is dried and concentrated to afford a mixture of C-17 epimers. Chromatography yields 17β-cyano 17α-acetoxy-estr-1,3,5(10)-triene-3-(methyl carboxylate).

(ii) Estr-1,3,5(10)-triene-17α-ol-3,17β-dicarboxylic Acid.

A solution of 17β-cyano-17α-acetoxy-estr-1,3,5(10)-triene-3-(methyl carboxylate) in methanol is cooled to 15° C. Dry HCl is bubbled into the solution and the mixture allowed to stand at room temperature for two hours. Solvent is then removed under reduced pressure. A mixture of 1:1 tetrahydrofuran:water is added followed by excess sodium hydroxide and the mixture is stirred at 40° C. for 24 hours, and then acidified and extracted with chloroform. Concentration of the organic solution and recrystallization from methanol affords estr-1,3,5(10)-triene-17α-ol-3,17β-dicarboxylic acid.

EXAMPLE 17

2′,3′-Tetrahydrofuran-2′-spiro-17-(1,3,5(10)-estratriene-3-carboxylic Acid)

The title compound is prepared according to Example 1 (i, iii, v) by substituting 2′,3′α-tetrahydrofuran-2′-spiro-17-(3-methoxy-1,3,5-estratriene), prepared according to Arth (J. Med. Chem. 6 617–618 (1963)), for estrone.

EXAMPLE 18

17β-(N,N-Diisopropylcarboxamide)-estr-1,3,5(10)-triene-3-thiocarboxylic Acid

A solution of 17β-(N,N-diisopropylcarboxamide)-estr-1,3,5(10)-triene-3-carboxylic acid (1 mmol) is suspended in 10 mL toluene and treated with 0.5 mL of oxalyl chloride for two hours. The resulting solution then is slowly added to a solution of THF and hydrogen sulfide through which hydrogen sulfide is being bubbled. The mixture is then diluted with ethyl acetate, washed with water, dried and concentrated. The residue is recrystallized from acetonitrile to yield the title compound.

EXAMPLE 19

17β-(N,N-Diisopropylcarboxamide)-estr-1,3,5(10),9(11)-tetraene-3-carboxylic Acid (i) N,N-Diisopropyl estr-1,3,5(10),9(11)-tetraene-3-ol-17β-carboxamide.

A solution of N,N-diisopropyl-estr-1,3,5(10)-triene-3-ol-17β-carboxamide (380 mg, 1 mmol) in 10 mL dioxane is treated with 2,3-dichloro-5,6-dicyano-1,4-benzoquinone (250 mg, 1.1 mmol) for two hours. The reaction mixture is diluted with ethyl acetate, washed with saturated aqueous NaHCO$_3$, dried, and concentrated. Chromatography of the residue yields N,N-diisopropyl estr-1,3,5(10),9(11)-tetraene-3-ol-17$\beta$-carboxamide.

(ii) 17$\beta$-(N,N-Diisopropylcarboxamide)-estr-1,3,5(10),9(11)-tetraene-3-carboxylic Acid.

The title compound is prepared according to Example 1 (i, iii, v) by substituting N,N-diisopropyl estr-1,3,5(10),9(11)-tetraene-3-ol-17$\beta$-carboxamide for estrone.

EXAMPLE 20

17$\beta$-(N,N-Diisopropylcarboxamide)-2-bromo-estr-1,3,5(10)-triene-3-carboxylic Acid and 17$\beta$-(N,N-Diisopropylcarboxamide)-4-bromo-estr-1,3,5(10)-triene-3-carboxylic Acid (i) N,N-diisopropyl-2-bromo-estr-1,3,5(10)-triene-3-ol-17$\beta$-carboxamide and N,N-Diisopropyl-4-bromo-estr-1,3,5(10-triene-3-ol-17$\beta$-carboxamide.

A solution of N,N-diisopropyl estr-1,3,5(10)-triene-3-ol-17$\beta$-carboxamide (1.85 g, 4.82 mmol) in 185 ml of warm acetic acid was cooled to 20° C. and 4.48 ml (4.82 mmol) of a 1.08 M solution of bromine in acetic acid was added slowly. After stirring at ambient temperature for 5 min, the reaction mixture was poured into ice water and extracted twice with dichloromethane. The combined dichloromethane extracts were washed twice with water, dried over anhydrous MgSO$_4$ and concentrated. Chromatography (silica gel, 2% followed by 5% ether in dichloromethane) afforded 0.39 g of N,N-diisopropyl-2-bromo-estr-1,3,5(10)-triene-3-ol-17$\beta$-carboxamide and 0.75 g of N,N-diisopropyl-4-bromo-estr-1,3,5(10)-triene-3-ol-17$\beta$-carboxamide.

(ii) 17$\beta$-(N,N-diisopropylcarboxamide)-2-bromo 3-(trifluoromethylsulfonate)-estr-1,3,5(10)-triene and 17$\beta$-(N,N-diisopropylcarboxamide)-4 bromo-3-(trifluoromethylsulfonate)-estr-1,3,5(10)-triene.

A solution of N,N-diisopropyl-2-bromoestr-1,3,5(10)-triene-3-ol-17$\beta$-carboxamide (0.393 g, 0.850 mmol) in dichloromethane (20 mL) was cooled with an ice bath and treated successively with lutidine (0.149 mL, 1.275 mmol), 4-dimethylaminopyridine (20.8 mg, 0.17 mmol) and trifluoromethane sulfonic anhydride (0.214 mL, 1.275 mmol). The reaction mixture was stirred at room temperature for two hours then concentrated at ambient temperature The residue was treated with ether and 10% HCl, then the organic layer was washed with water followed by 5% NaHCO$_3$, dried and concentrated to yield 0.481 g (95%) of 17$\beta$-(N,N-diisopropylcarboxamide)-2-bromo-3-(trifluoromethylsulfonate)-estr-1,3,5(10)-triene.

Substitution of (N,N-diisopropyl-4-bromo-estr-1,3,5(10)-triene-3-ol-17$\beta$-carboxamide for (N,N-diisopropyl-2-bromo-estr-1,3,5(10)-triene-3-ol-17$\beta$-carboxamide afforded a 99% yield of 17$\beta$-(N,N-diisopropylcarboxamide)-4-bromo 3-(trifluoromethylsulfonate)-estr-1,3,5(10)-triene.

(iii) 2-Bromo-3-carbomethoxy-17$\beta$-(N,N-diisopropylcarboxamide-estr-1,3,5(10)-triene and 4-Bromo-3-carbomethoxy-17$\beta$-(N,N-diisopropylcarboxamide) estr-1,3,5(10)-triene.

The title compounds were prepared according to Example 1(iii) by substituting 17$\beta$-(N,N-diisopropylcarboxamide)-2-bromo-3-(trifluoromethylsulfonate)-estr-1,3,5(10)-triene and 17$\beta$-(N,N-diisopropylcarboxamide)-4-bromo-3-(trifluoromethylsulfonate)-estr-1,3,5(10)-triene for 17$\beta$-(N,N-diisopropylcarboxamide)-3-(trifluoromethylsulfonate)-estr-1,3,5(10),16-tetraene.

(iv) 17$\beta$-(N,N-Diisopropylcarboxamide)-2-bromo-estr-1,3,5(10)-triene-3-carboxylic Acid and 17$\beta$-(N,N-Diisopropylcarboxamide-4-bromo-estr-1,3,5(10)-triene-3-carboxylic Acid.

Substitution of 2-bromo-3-carbomethoxy-17$\beta$-(N,N-diisopropylcarboxamide)-estr-1,3,5(10) triene for 3-carbomethoxy-17$\beta$-(N,N-diisopropylcarboxamide)-estr-1,3,5(10)-triene as in Example 1(v) yielded 17$\beta$-(N,N-diisopropylcarboxamide)-2-bromo-estr1,3,5(10)-triene-3-carboxylic acid, m.p.294°–300° C.

Substitution of 4-bromo-3-carbomethoxy-17$\beta$-(N,N-diisopropylcarboxamide)-estr-1,3,5(10) triene for 3-carbomethoxy-17$\beta$-(N,N-diisopropylcarboxamide)-estr-1,3,5(10)-triene as in Example 1(v) yielded 17$\beta$-(N,N-diisopropylcarboxamide)-4-bromo-estr-1,3,5(10)-triene-3-carboxylic acid, m.p. 276°–280° C.

EXAMPLE 21

17$\beta$-(N,N-Diisopropylcarboxamide)-2,4-dibromo-estr-1,3,5(10)-triene-3-carboxylic Acid (i) N,N-Diisopropyl-2,4-dibromo-estr-1,3,5(10)-triene 3-ol-17$\beta$-carboxamide.

The title compound is prepared according to Example 20(i) by reacting N,N-diisopropyl-estr-1,3,5(10)-triene-3-ol-17$\beta$-carboxamide with 2.0 equivalents of bromine.

(ii) 17$\beta$-(N,N-Diisopropylcarboxamide)-2,4-dibromo-estr-1,3,5(10)-triene-3-carboxylic Acid.

The title compound is prepared to Example 20 (ii, iii and iv) by substituting N,N-diisopropyl-2,4-dibromo-estr-1,3,5(10)-triene-3-ol-17$\beta$-carboxamide for N,N-diisopropyl-2-bromo-estr-1,3,5(10)-triene-3-ol-17$\beta$-carboxamide.

EXAMPLE 22

17$\beta$-(N,N-Diisopropylcarboxamide)-2-cyano-estr-1,3,5(10)-triene-3-carboxylic Acid and 17$\beta$-(N,N-Diisopropylcarboxamide-4-cyano-estr-1,3,5(10)-triene-3-carboxylic Acid (i) 3-Carbomethoxy-2-cyano-17$\beta$-(N,N-diisopropylcarboxamide)-estr-1,3,5(10)-triene.

A mixture of 2-bromo-3-carbomethoxy-17$\beta$-(N,N-diisopropylcarboxamide)-estr-1,3,5(10)-triene (33.2 mg, 0.0658 mmol), copper(I) cyanide (10.6 mg, 0.118 mmol) and N-methylpyrrolidinone (1.0 mL) was heated in an oil bath at 180° C. under an argon atmosphere for one hour. The reaction mixture was cooled to room temperature and treated with an aqueous solution of ethylene diamine, then extracted twice with ethyl acetate The ethyl acetate extracts were washed once with a 10% aqueous solution of sodium cyanide and twice with water Concentration yielded 25.7 mg 87%) of 3-carbomethoxy-2-cyano-17$\beta$-(N,N-diisopropylcarboxamide)-estr-1,3,5(10)-triene.

(ii) 3-carbomethoxy-4-cyano-17$\beta$-(N,N-diisopropylcarboxamide)-estr-1,3,5(10)-triene.

A mixture of 4-bromo-3-carbomethoxy-17$\beta$-(N,N-diisopropylcarboxamide)-estr-1,3,5(10)-triene mg, 0.272 mmol), copper(I) cyanide (43.8 mg, 0.489 mmol) and N-methylpyrrolidinone (1.5 mL) was heated in an oil bath at 180° C. under an argon atmosphere for one hour. The reaction mixture was cooled to room temperature and treated with an aqueous solution of ethylene diamine, then extracted twice with ethyl acetate. The ethyl acetate extracts were washed once with a 10% aqueous solution of sodium cyanide and twice with water. Concentration followed by chromatography (silica gel, 10% ether in dichloromethane) yielded 85 mg (70%) of 3-carbomethoxy-4-cyano-17β-(N,N-diisopropylcarboxamide)-estr-1,3,5(10)-triene.

(iii) 17β-(N,N-Diisopropylcarboxamide)-2-cyano-estr-1,3,5(10) triene-3-carboxylic Acid and 17β-(N,N-Diisopropylcarboxamide-4-cyano-estr-1,3,5(10)-triene-3-carboxylic Acid.

Substitution of 3-carbomethoxy-2-cyano-(N,N-diisopropylcarboxamide)-estr-1,3,5(10)-triene for carbomethoxy-17β-(N,N-diisopropylcarboxamide)-estr-1,3,5(10)-triene as in Example 1(v) yielded 17β-(N,N-diisopropylcarboxamide)-2-cyano-estr-1,3,5(10)-triene-3-carboxylic acid, m.p. 270°–273° C.;

Substitution of 3-carbomethoxy-4-cyano-17β-(N,N-diisopropylcarboxamide-estr-1,3,5(10)-triene for 3-carbomethoxy-17β-(N,N-diisopropylcarboxamide)-estr-1,3,5(10)-triene as in Example 1(v) yielded 17β-(N,N-diisopropylcarboxamide)-4-cyano-estr-1,3,5(10)-triene-3-carboxylic acid, m.p. 240°–242° C.

EXAMPLE 23

17β-(N,N-Diisopropylcarboxamide)-2-formyl-estr-1,3,5(10)-triene-3-carboxylic Acid (i) 3-Carbomethoxy-2-formyl-17β-(N,N-diisopropylcarboxamide)-estr-1,3,5(10)-triene.

The title compound is prepared by reaction of 3-carbomethoxy-2-cyano-17β-(N,N-diisopropylcarboxamide)-estr- 1,3,5(10)-triene with Raney nickel alloy and formic acid according to the procedure of Staskun (J. Chem. Soc. 5880 (1964)).

(ii) 17β-(N,N-Diisopropylcarboxamide)-2-formyl-estr-1,3,5(10 triene-3-carboxylic Acid.

Substitution of 3-carbomethoxy-2-formyl-17β-(N,N-diisopropylcarboxamide)-estr-1,3,5(10)-triene for 3-carbomethoxy-17β-(N,N-diisopropylcarboxamide)-estr-1,3,5(10)-triene as in Example 1(v) yields the title compound.

EXAMPLE 24

17β-(N,N-Diisopropylcarboxamide)-2-fluoro-estr-1,3,5(10)-triene-3-carboxylic Acid and 17β-(N,N-Diisopropylcarboxamide-4-fluoro-estr-1,3,5(10)-triene-3-carboxylic Acid The title compounds are prepared according to Example 8(i and ii) by substituting 2-fluoro-3-methyl-estrone and fluoro 3-methyl-estrone (prepared according to the procedures described by Neeman, J. Chem. Soc Perkin I 2297 (1972) and J. Chem Soc. Perkin I 2300 (1972)) for 3-methyl-estrone.

EXAMPLE 25

17β-N,N-Diisopropylcarboxamide-estr-1,3,5(10)-triene-2,3-dicarboxylic Acid (i) N,N-Diisopropyl-2-bromo-3-methoxy-estr-1,3,5(10)-triene-17β-carboxamide.

A mixture of N,N-diisopropyl-2-bromo-estr-1,3,5(10)-triene-3 ol-17β-carboxamide (188 mg, 0.407 mmol), dimethyl sulfate (76.9 mL, 0.814 mmol), powdered anhydrous potassium carbonate (112 mg, 0.814 mmol) and acetone (10 mL) was refluxed under an argon atmosphere for 1.25 hours. The cooled reaction mixture was diluted with water and extracted with dichloromethane. The dichloromethane extract was washed with water, dried and concentrated to 162 mg (84%) of the title compound.

(ii) 17β-(N,N-Diisopropylcarboxamide-3-methoxy-estr-1,3,5(10)-triene-2-carboxylic Acid.

A solution of N,N-diisopropyl-2-bromo-3-methoxy-estr-1,3,5(10)-triene-17β-carboxamide (151 mg, 0.317 mmol) in tetrahydrofuran (5 mL) was added dropwise at −78° C. to a solution prepared from 0.285 mL (0.713 mmol) of 2.5M n-BuLi in hexane and tetrahydrofuran (5 mL). Upon completion of the addition the reaction was stirred at −78° C. for 5 min, then powdered dry ice ($CO_2$) was added After allowing to slowly warm to room temperature, the mixture was poured into water, acidified with dilute HCl and extracted twice with dichloromethane. The dichloromethane extracts were washed with water, dried and concentrated to 125 mg (89%) of the title compound.

(iii) 2-Carbomethoxy-3-methoxy-17β-(N,N-diisopropylcarboxamide)-estr-1,3,5(10)-triene.

The title compound was prepared by treating 17β-(N,N-diisopropylcarboxamide)-3-methoxy-estr-1,3,5(10)-triene-2-carboxylic acid with methanol and HCl.

(iv) N,N-Diisopropyl-2-carbomethoxy-estr-1,3,5(10)-triene-3-ol-17β-carboxamide.

A solution of 2-carbomethoxy-3-methoxy-17β-(N,N-diisopropylcarboxamide)-estr-1,3,5(10)-triene (138 mg, 0.303 mmol) in dichloromethane (5 mL) was cooled with an ice bath and 0.333 mL (0.333 mmol) of a 1.0M solution of boron tribromide in dichloromethane was added slowly. After stirring in the cold for 2.5 hours, excess methanol was added slowly and the mixture concentrated to dryness. The residue was redissolved in methanol concentrated and purified by chromatography (silica gel, 5% ether in dichloromethane) to yield 38.4 mg (29%) of the title compound.

(v) 17β-(N,N-Diisopropylcarboxamide)-2-carbomethoxy-3-(trifluoromethylsulfonate)-estr-1,3,5(10)-triene.

A solution of N,N-diisopropyl-2-carbomethoxy-estr-1,3,5(10)-triene-3-ol-17β-carboxamide (24.3 mg, 0.0550 mmol) in tetrahydrofuran (2 mL) was added to a cold mixture of excess sodium hydride in tetrahydrofuran (2 mL) and the resultant mixture stirred at room temperature 0.5 hours. A solution of N-phenyltrifluoromethanesulfonimide (31.6) mg, 0.0885 mmol) in tetrahydrofuran (2 mL) was added and the mixture was heated in an oil bath at 40° C. for 4 hours. The mixture was diluted with dichloromethane, washed twice with 5% $NaHCO_3$, dried and concentrated to 26.1 mg (83%) of the title compound.

(vi) 2,3-Bis(carbomethoxy)-17β-(N,N-diisopropylcarboxamide)-estr-1,3,5(10)-triene.

The title compound was prepared as in Example 1(iii) by substituting 17β-(N,N-diisopropylcarboxamide)-2-carbomethoxy-3 (trifluoromethylsulfonate)-estr-1,3,5(10)-triene for 17β-(N,N-diisopropylcarboxamide)-3-(trifluoromethylsulfonate)-estr-1,3,5(10),16-tetraene.

(vii) 17β-N,N-Diisopropylcarboxamide-estr-1,3,5(10)-triene-2,3-dicarboxylic Acid.

Substitution of 2,3 bis(carbomethoxy)-17β-(N,N-diisopropylcarboxamide)-estr-1,3,5(10)-triene for 3-carbomethoxy-17β-(N,N-diisopropylcarboxamide)-estr-1,3,5(10)-triene as in Example 1(v) yields the title compound.

EXAMPLE 26

17β-(N,N-Diisopropylcarboxamide)-2-amino-estr-1,3,5(10)-triene-3-carboxylic Acid and 17β-(N,N-Diisopropylcarboxamide)-4-amino-estr-1,3,5(10)-triene-3-carboxylic Acid (i) N,N-Diisopropyl-2-nitro-estr-1,3,5(10)-triene-3-ol-17β-carboxamide and N,N-Diisopropyl-4-nitro estr-1,3,5(10)-triene-3-ol-17β-carboxamide.

A solution of N,N-diisopropyl-estr-1,3,5(10)-triene-3-ol-17β-carboxamide (141 mg, 0.368 mmol) in boiling acetic acid (7 mL) was slowly cooled to 75° C. and treated with a solution of concentrated nitric acid (24.8 μL) in water (1.4 mL) containing a catalytic unit of sodium nitrite. The reaction mixture was allowed to slowly cool to room temperature, then was diluted with water and extracted with ethyl acetate. The extract was washed thoroughly with water, dried, concentrated and purified by chromatography (silica gel, dichloromethane containing 5 to 10% ether) affording 55.2 mg (35%, mp 143.5°–144.5° C.) of N,N-diisopropyl-2-nitro-estr-1,3,5(10)-triene-3-ol-17β-carboxamide and 32.2 mg (20%, mp 239°–241° C.) of N,N-diisopropyl-4-nitro-estr-1,3,5(10)-triene-3-ol-17β-carboxamide.

(ii) 17β-(N,N-Diisopropylcarboxamide)-2-nitro-3-(trifluoromethlysulfonate)-estr-1,3,5(10)-triene and 17β-(N,N-Diisopropylcarboxamide-4-nitro-3-(trifluoromethylsulfonate)-estr-1,3,5(10)-triene.

The title compounds are prepared according to Example 1(i) by substituting N,N-diisopropyl-2-nitro-estr-1,3,5(10)-triene-3-ol-17β-carboxamide and N,N-diisopropyl-4-nitro-estr-1,3,5(10)-triene-3-ol-17β-carboxamide for estrone.

(iii) 17β-(N,N-Diisopropylcarboxamide)-2-trifluoroacetamide-3-(trifluoromethylsulfonate)-estr-1,3,5(10)-triene and 17β-(N,N-Diisopropylcarboxamide)-4-trifluoroacetamide-3-(trifluoromethylsulfonate)-estr-1,3,5(10)-triene.

The title compounds are prepared by reduction with hydrogen catalyzed by Raney Nickel followed by reaction with trifluoroacetic anhydride.

(iv) 3-Carbomethoxy-2-trifluoroacetamido-17β-(N,N-diisopropylcarboxamide)-estr-1,3,5(10)-triene and 3-Carbomethoxy-4-trifluoroacetamide-17β-(N,N-diisopropylcarboxamide)-estr-1,3,5(10)-triene.

The title compounds are prepared according to Example 1(iii) by substituting 17β-(N,N-diisopropylcarboxamide) 2-trifluoroacetamide-3-(trifluoromethylsulfonate)-estr-1,3,5(10)-triene and 17β-(N,N-diisopropylcarboxamide)-4-trifluoroacetamido-3-(trifluoromethylsulfonate)-estr-1,3,5(10)-triene for 17β-(N,N-diisopropylcarboxamide)-3-(trifluoromethylsulfonate)-estr-1,3,5(10),16-tetraene.

(v) 17β-(N,N-Diisopropylcarboxamide)-2-amino-estr-1,3,5(10)-triene-3-carboxylic Acid and 17β-(N,N-Diisopropylcarboxamide)-4-amino-estr-1,3,5(10)-triene-3-carboxylic Acid.

The title compounds are prepared according to Example 1(v) by substituting 3-carbomethoxy-2-trifluoroacetamide-17β-(N,N-diisopropylcarboxamide)-estr-1,3,5(10)-triene and 3-carbomethoxy-4-trifluoroacetamido-17β-(N,N-diisopropylcarboxamide)-estr-1,3,5(10)-triene for 3-carbomethoxy-17β-(N,N-diisopropylcarboxamide)-estr-1,3,5(10)-triene.

EXAMPLE 27

17β-(N,N-Diisopropylcarboxamide)-2-hydroxy-estr-1,3,5(10)-triene-3-carboxylic Acid The title compound is prepared from 17β-(N,N-diisopropylcarboxamide)-2-amino-estr-1,3,5(10)-triene-3-carboxylic acid by the method of Ungnade (*Org. Syn. Coll. Vol.* 3, 130).

EXAMPLE 28

17β-(N,N-Diisopropylcarboxamide)-2-nitro-estr-1,3,5(10)-triene-3-carboxylic Acid The title compound is prepared from 17β-(N,N-diisopropylcarboxamide)-2-amino estr-1,3,5(10)-triene-3-carboxylic acid by the method of Pagano (*Org. Syn. Coll. Vol.* 5, 367).

EXAMPLE 29

17β-(N,N-Diisopropylcarboxamide)-1-bromo-estr-1,3,5(10)-triene-3-carboxylic Acid (i) N,N-Diisopropyl-3-methoxy-4-nitro-estr-1,3,5(10)-triene-17β-carboxamide.

The title compound is prepared according to Example 25(i) by substituting N,N-diisopropyl-nitro-estr-1,3,5(10)-triene-3-ol-17β-carboxamide for N,N-diisopropyl-2-bromo-estr-1,3,5(10)-triene-3-ol-17β-carboxamide.

(ii) N,N-Diisopropyl-1-bromo estr-1,3,5(10)-triene-3-ol-17β-carboxamide.

The title compound is prepared according to the method of Hylarides (*J. Org. Chem.* 49, 2744 (1984)) by substituting N,N-diisopropyl-3-methoxy-4-nitro-estr-1,3,5(10)-triene-17β-carboxamide for 3-methyl-4-nitro estrone.

(iii) 17β-(N,N-Diisopropylcarboxamide)-1-bromo-estr-1,3,5(10)-triene-3-carboxylic Acid.

The title compound is prepared according to Example 1(i, iii, and v) by substituting N,N-diisopropyl-1-bromo-estr-1,3,5(10)-triene-3-ol-17β-carboxamide for estrone.

EXAMPLE 30

3-Ethenyl-estr-1,3,5(10)-triene-17β-(N-t-butylcarboxamide)

A mixture of 3-(trifluoromethylsulfonate)-estr-1,3,5(10)-triene-17β-(N t-butylcarboxamide) (1.0 g), tributylvinylstannane (0.63 mL), lithium chloride (260 mg), bis(triphenylphosphine)palladium (II) chloride (80 mg), 2,6-di-t-butyl-4-methylpyridine (20 mg), and DMF (15 mL) and washed with water and brine, dried over magnesium sulfate, and concentrated to a brown residue. Chromatography afforded the title compound (485 mg, 65%) as a white solid, m.p. 66°–69° C.

3-(2'-Hydroxyethyl)-estr-1,3,5(10)-triene-17β-(N-t-butylcarboxamide)

A solution of 3-ethenyl-estr-1,3,5(10)-triene-17β-(N-t-butylcarboxamide) (100 mg) in THF (2 mL) was treated with a solution of 9-borobicyclononane (1.0 mL, 0.5M in THF). The resulting solution was heated at reflux for 1.5 hours, cooled to room temperature, and treated with absolute ethanol (4 mL), 6M KOH (2 drops), and 30% hydrogen peroxide (0.4 mL). The reaction mixture was then heated to 50° C. for 1.5 hours, cooled, and partitioned between ethyl acetate and water. The aqueous layer was extracted with ethyl acetate and the combined organic layers were washed with brine, dried over magnesium sulfate, and concentrated to provide 105 mg of the title compound as a white foam.

17β-(N t-butylcarboxamide)-estr-1,3,5(10)-triene-3-acetic acid

A solution of 3-(2'-hydroxyethyl)-estr-1,3,5(10)-triene-17β-(N-t butylcarboxamide) (105 mg) in acetone (15 mL) was cooled to −5° C. and treated with Jones reagent (0.6 mL, 1.5M) for 2 hours. The reaction was then quenched by the addition of 2 propanol (10 mL) and water (15 mL). The mixture was then extracted with dichloromethane and the extracts washed with brine, dried over magnesium sulfate, and concentrated to a viscous yellow oil. Column chromatography provided the pure title compound (60 mg) as a white solid, m.p. 119°–123° C.

EXAMPLE 31

17β-(N,N-diisopropylcarboxamide)-estr-1,3,5(10)-triene-3-acetic acid

Substitution of 3-(trifluoromethylsulfonate)-estr-1,3,5(10)-triene-17β-(N,N-diisopropylcarboxamide) for 3-(trifluoromethyl-sulfonate)-estr-1,3,5(10)-triene-17β-(N-t-butylcarboxamide) in Example 30 provides the title compound, m.p. 125°–127° C.

EXAMPLE 32

Using the appropriate starting 3-trifluoromethylsulfonate derivative in the procedure of Example 30 the following compounds are obtained:

17β-(N,N-diisopropylcarboxamide)-estr-1,3,5(10),6-tetraene-3-acetic acid

17β-(N,N-diisopropylcarboxamide)-estr-1,3,5(10),6,8-pentaene-3-acetic acid

17β-(N,N-diisopropylcarboxamide)-2-methyl-estr-1,3,5(10)-triene-3-acetic acid

EXAMPLE 33

An oral dosage form for administering Formula (I) compounds is produced by screening, mixing, and filling into hard gelatin capsules the ingredients in the proportions shown in Table III, below.

TABLE III

| Ingredients | Amounts |
| --- | --- |
| 17β-(N,N-Diisopropylcarboxamide)-estr-1,3,5(10)-triene-3-carboxylic Acid | 50 mg |
| magnesium stearate | 5 mg |
| lactose | 75 mg |

EXAMPLE 34

The sucrose, calcium sulfate dihydrate and Formula (I) compound shown in Table IV below, are mixed and granulated in the proportions shown with a 10% gelatin solution. The wet granules are screened, dried, mixed with the starch, talc and stearic acid, screened and compressed into a tablet.

TABLE IV

| Ingredients | Amounts |
| --- | --- |
| 17β-(N-tert-Butylcarboxamide)-estr-1,3,5(10)-triene-3-carboxylic | 100 mg |
| calcium sulfate dihydrate | 150 mg |
| sucrose | 20 mg |
| starch | 10 mg |
| talc | 5 mg |
| stearic acid | 3 mg |

EXAMPLE 35

17β-(N,N-Diisopropylcarboxamide)-estr-1,3,5(10),16-tetraene-3-carboxylic acid sodium salt, 75 mg, is dispersed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the formula:

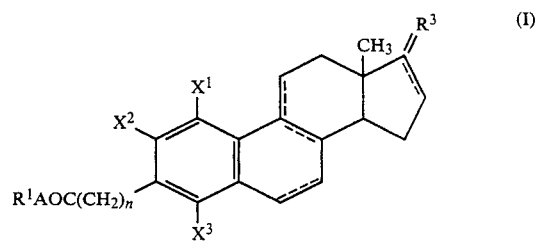

in which:

the B, C, and D rings have optional double bonds where indicated by the broken lines, provided that the C ring does not have a double bond when the B ring has a $C_8$–$C_9$ double bond and the D ring does not have a $C_{16}$–$C_{17}$ double bond when $R^3$ represents two substituents or a divalent substituent;

$X^1$, $X^2$, and $X^3$ are any accessible combination of H, Cl, F, Br, I, CF, or $C_{1-6}$alkyl OH, $C_{1-6}$alkoxy, CN, $NO_2$, $N(R^1)_2$, CHO, or $CO_2R^1$;

A is O or S;

n is 0 or 1;

$R^1$ each independently is H or $C_{1-8}$alkyl; and $R^3$ is (1) α-hydrogen, α-hydroxyl, or α-acetoxy and/or (a)

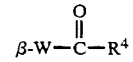

where W is a bond or $C_{1-12}$alkyl, and $R^4$ is (i) hydrogen, (ii) hydroxyl, (iii) $C_{1-8}$alkyl, (iv) hydroxy $C_{1-8}$alkyl, (v) $C_{1-8}$alkoxy, (vi) $NR^5R^6$, where $R^5$ and $R^6$ are each independently selected from hydrogen, $C_{1-8}$alkyl, $C_{3-6}$cycloalkyl, phenyl; or $R^5$ and $R^6$ taken together with the nitrogen to which they are attached represent a 5–6 membered saturated ring comprising up to one other heteroatom selected from oxygen and nitrogen, or (vii) $OR^7$, where $R^7$ is alkali metal, $C_{1-18}$alkyl, or benzyl, or (b) β-Alk-$OR^8$, where Alk is $C_{1-12}$alkyl, and $R^8$ is (i) phenyl$C_{1-6}$alkylcarbonyl, (ii) $C_{5-10}$cycloalkylcarbonyl,
(iii) benzoyl,
(iv) $C_{1-8}$alkoxycarbonyl,
(v) amino, or $C_{1-8}$alkyl substituted amino, carbonyl, or
(vi) $C_{1-8}$alkyl, (2) =CH—W—CO—$R^4$ or =CH—W—$OR^8$, where W is a bond or $C_{1-12}$alkyl and $R^4$ and $R^8$ have the same meaning as above and $R^8$ also is $C_{1-20}$alkylcarbonyl;

(3)

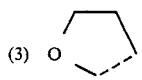

where the dashed bond replaces the 17-α-hydrogen, (4) α-hydrogen and β-NHCOR$^9$ where $R^9$ is $C_{1-12}$alkyl or β-$NR^5R^6$ where $R^5$ and $R^6$ have the same meaning as above, (5) α-hydrogen and β-cyano,
(6) α-hydrogen and β-tetrazolyl, or
(7) keto;

or a pharmaceutically acceptable salt thereof; except the compound in which:
$R^1$ is $CH_3$, n is 0, A is O, and $R^3$ is keto.

2. A compound of claim 1 having the following

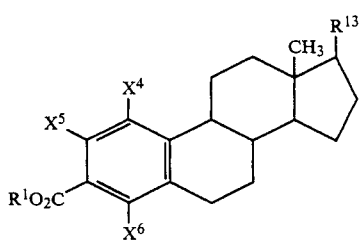

in which:
$X^4$, $X^5$, and $X^6$ independently are H, halo, or $C_{1-6}$alkyl,
$R^1$ is H or $C_{1-8}$alkyl; and
$R^{13}$ is
(a) CH(CH CH$_2$OR$^1$, or
(b) CONR$^1$R$^1$;
or a pharmaceutically acceptable salt thereof.

3. A compound of claim 2 wherein the $R^1$ substituent at position 3 is H.

4. A compound of claim 3 that is 17β-(N,N-diisopropylcarboxamide)-estr-1,3,5(10)-triene-3-carboxylic acid or a salt thereof.

5. A compound of claim 3 that is 17β-(N-tert-butylcarboxamide)-estr-1,3,5(10)-triene-3-carboxylic acid or a salt thereof.

6. A compound of claim 1 that is
17β-(N,N-diisopropylcarboxamide-2-methyl-estr-1,3,5(10)-triene-3-carboxylic acid or salt thereof,
17β-(N,N-diisopropylcarboxamide-4-methyl-estr-1,3,5(10)-triene-3-carboxylic acid or a salt thereof,
17β-(N,N-diisopropylcarboxamide-2-chloro-estr-1,3,5(10)-triene-3-carboxylic acid or a salt thereof,
17β-(N N-diisopropylcarboxamide)-4-chloro-estr-1,3,5(10) triene-3-carboxylic acid or a salt thereof,
17β-(N,N-diisopropylcarboxamide)-estr-1,3,5(10),16 tetraene-3-carboxylic acid or a salt thereof,
17β-(N-tert-butylcarboxamide)-estr-1,3,5(10),16-tetraene-3-carboxylic acid or a salt thereof,
17β-(N,N-diisopropylcarboxamide)-estr-1,3,5(10),6,8,-pentaene-3-carboxylic acid or a salt thereof,
17β-(N,N-diisopropylcarboxamide)-estr-1,3,5(10),6-tetraene-3-carboxylic acid or a salt thereof.

7. A compound of claim 1 in which the B, C and D rings have no double bonds; n is 1; A is O; $X^1$, $X^2$ and $X^3$ are H and $R^3$ is β-CH(CH$_3$)CH$_2$OR$^1$ or β-CONR$^1$R$^1$.

8. A compound of claim 7 that is 17β-(N,N-diisopropylcarboxamide)-estr-1,3,5(10)-triene-3-acetic acid or a pharmaceutically acceptable salt thereof or 17β-(N-t-butylcarboxamide)-estr-1,3,5(10)-triene-3-acetic acid or a pharmaceutically acceptable salt thereof.

9. A pharmaceutical composition comprising a suitable pharmaceutical carrier and a compound of claim 1 in which $R^1$ is H.

10. A composition of claim 9 wherein the compound is
17β-(N-tert-butylcarboxamide)-estr-1,3,5(10) triene-3-carboxylic acid or a salt thereof,
17β-(N,N-diisopropylcarboxamide)-estr-1,3,5(10)-triene-3-carboxylic acid or a salt thereof,
17β-(N,N-diisopropylcarboxamide-2-methyl-estr-1,3,5(10)-triene-3-carboxylic acid or a salt thereof,
17β-(N,N-diisopropylcarboxamide-4-methyl-estr-1,3,5(10)-triene-3-carboxylic acid or a salt thereof,
17β-(N,N-Diisopropylcarboxamide-2-chloro-estr-1,3,5(10)-triene-3-carboxylic acid or a salt thereof,
17β-(N,N-diisopropylcarboxamide)-4-chloro-estr-1,3,5(10)-triene-3-carboxylic acid or a salt thereof,
17β-(N,N-diisopropylcarboxamide)-estr-1,3,5(10),16-tetraene-3-carboxylic acid or a salt thereof,
17β-(N-tert butylcarboxamide)-estr-1,3,5(10),16-tetraene-3-carboxylic acid or a salt thereof, 17β-(N,N-diisopropylcarboxamide)-estr-1,3,5(10),6,8,-pentaene-3-carboxylic acid or a salt thereof,
17β-(N,N-diisopropylcarboxamide)-estr-1,3,5(10),6 tetraene-3-carboxylic acid or a salt thereof,
17β-(N,N-diisopropylcarboxamide)-estr-1,3,5(10)triene-3-acetic acid or a salt thereof, or
17β-(N-t-butylcarboxamide)-estr-1,3,5(10)-triene-3-acetic acid or a salt thereof.

11. A method of inhibiting steroid 5-α-reductase activity in a subject that comprises administering internally to the subject an effective amount of a compound of claim 1 in which $R^1$ is H.

12. A method of claim 11 wherein the compound is
17β-(N-tert-butylcarboxamide)-estr-1,3,5(10)-triene-3-carboxylic acid or a salt thereof,
17β-(N,N-diisopropylcarboxamide)-estr-1,3,5(10)-triene-3-carboxylic acid or a salt thereof,
17β-(N,N-diisopropyl-carboxamide-2-methyl-estr-1,3,5(10)-triene-3-carboxylic acid or a salt thereof,
17β-(N,N-diisopropylcarboxamide-4-methyl-estr-1,3,5(10)-triene-3-carboxylic acid or a salt thereof,
17β-(N,N-diisopropylcarboxamide-2-chloro-estr-1,3,5(10)-triene-3-carboxylic acid or a salt thereof,
17β-(N,N-diisopropylcarboxamide)-4-chloro-estr-1,3,5(10)-triene-3-carboxylic acid or a salt thereof,
17β-(N,N-diisopropylcarboxamide)-estr-1,3,5(10),16-tetraene-3-carboxylic acid or a salt thereof,
17β-(N tert-butylcarboxamide)-estr-1,3,5(10),16-tetraene-3-carboxylic acid or a salt thereof, 17β-(N,N-diisopropylcarboxamide)-estr-1,3,5(10),6,8,pentaene-3-carboxylic acid or a salt thereof, or 17β-(N,N-diisopropylcarboxamide)-estr-1,3,5(10),6-tetraene-3-carboxylic acid or a salt thereof, 17β-(N,N-diisopropylcarboxamide)-estr-1,3,5(10)-triene-3-acetic acid or a salt thereof, 17β-(N t-butylcarboxamide)estr-1,3,5(10)-triene-3-acetic acid or a salt thereof.

13. A method of reducing prostate size in a subject that comprises administering to a subject an effective amount of a compound of claim 1 in which $R^1$ is H.

14. A method of claim 13 wherein the compound is 17β-(N-tert-butylcarboxamide)-ester-1,3,5(10)-triene-3-carboxylic acid or a salt thereof.

* * * * *